United States Patent [19]

Erian

[11] Patent Number: 4,612,800
[45] Date of Patent: Sep. 23, 1986

[54] SLURRY VISCOMETER

[75] Inventor: Fadel F. Erian, Katy, Tex.

[73] Assignee: Shell Mining Company, Houston, Tex.

[21] Appl. No.: 720,845

[22] Filed: Apr. 8, 1985

[51] Int. Cl.[4] .......................................... G01N 11/16
[52] U.S. Cl. ...................................................... 73/54
[58] Field of Search ............................................. 73/54

[56] References Cited

U.S. PATENT DOCUMENTS

| 3,017,767 | 1/1962 | Mossberg | 73/54 |
| 3,163,172 | 12/1964 | Buzzard | 73/54 X |
| 3,903,731 | 9/1975 | Sieben | 73/54 |
| 4,151,744 | 5/1979 | Hemmings | 73/54 |
| 4,184,364 | 1/1980 | Du Bae | 73/54 |

FOREIGN PATENT DOCUMENTS

| 2622375 | 1/1977 | Fed. Rep. of Germany | 73/54 |
| 179409 | 5/1962 | Sweden | 73/54 |

Primary Examiner—Stewart J. Levy
Assistant Examiner—Joseph W. Roskos

[57] ABSTRACT

An apparatus and method are provided for measuring apparent viscosities of conventional as well as unconventional slurries. In particular, slurries which utilize supercritical liquid $CO_2$ as a carrier fluid can be tested at a variety of concentrations and particle size distributions. The method is capable of forming the slurry mixture and maintaining the solids in relatively uniform suspension. A sensing element, which is a vibrating-rod, is used as a viscosity detector.

16 Claims, 5 Drawing Figures

SLURRY VISCOMETER

BACKGROUND OF THE INVENTION

Viscosities of slurries which are stable under normal atmospheric conditions can be obtained in a variety of ways. For instance, if the solids are finely ground and can be maintained in relatively uniform suspension for sufficient times, capillary or Couette-type viscometers would be suitable. Conversely, if the particles are so heavy that settling would take place during the measurement process, or, are large relative to the capillary tube diameter or the gap size between the stationary and rotating cylinders of the Couette viscometer, such instruments would be unsuitable. In these cases costly pipeloop systems must be constructed, and viscosities of either Newtonian or non-Newtonian slurries inferred from pressure drop data. If a variety of solids, carrier fluids, concentrations and particle size distributions are to be tested, time and manpower commitments can be substantial.

Obtaining viscosities of unconventional mixtures, such as coal-liquid $CO_2$ slurries, is considerably more difficult. None of the standard, commercially available instruments is particularly suited for this application. As above indicated, the only feasible way of obtaining this type of information is by inference from pressure drop data. With liquid $CO_2$ as the carrier liquid, such data can be obtained only from a costly high pressure flow loop.

Commercial vibrating-rod sensors initially appeared to provide a potential answer to slurry viscosity measurement problems of this type. The sensor is commonly used for monitoring fluid viscosities in field applications. While the vibrating-rod sensor has certain unique features capable of overcoming most of the drawbacks which rendered the use of other viscometers impractical for the above-described measurements, it was nonetheless necessary to provide a special apparatus as described hereinafter which utilizes the unique features of this sensor to obtain viscosity data of slurries which are made with high vapor pressure liquids such as $CO_2$.

Applicant is not aware of any prior art which, in his judgment as one skilled in the art of measuring slurry viscosities, would anticipate or render obvious this novel slurry measurement technique of the present invention.

SUMMARY OF THE INVENTION

The primary purpose of the present invention is to provide a method and apparatus for measuring apparent viscosities of conventional as well as unconventional slurries, in particular, slurries which utilize supercritical liquid $CO_2$ or similar high vapor pressure fluids such as liquefied petroleum gas and similar hydrocarbons as a carrier fluid for particulate material such as coal. Accordingly, the present invention provides an instrument for measuring slurry viscosity, comprising, a vessel capable of withstanding elevated pressures and defining an internal closed loop flow path; means for flowing the slurry in the flow path; and means for measuring the viscosity of the slurry as the slurry flows in the flow path. Preferably the internal closed loop flow path is formed by a chamber within the vessel, the chamber having a top, bottom and sides, with the top and bottom being at least partially open and the sides being at least partially spaced from the vessel. Preferably, the means for flowing and simultaneous mixing of the slurry is at least one propeller located within the chamber. More preferably, the means for flowing and simultaneous mixing of the slurry is two or more propellers, some located within the chamber and at least one located outside of the chamber at a location where the flow path enters the vessel. Also more preferably, the means for measuring the viscosity of the slurry is a vibrating-rod viscosity sensor.

The present invention also provides a method for measuring slurry viscosity, comprising, flowing the slurry in a closed loop flow path; and measuring the viscosity of the slurry as the slurry flows in the flow path. Preferably, the slurry is flowed through a chamber within a vessel and between the chamber and the vessel. More preferably, a vibrating-rod sensor is inserted into the flowing slurry and the viscosity of the slurry is correlated to the amplitude of vibration of the rod. Also preferably, the slurry is flowed by means of at least one propeller located inside the chamber. More preferably, the slurry is flowed by means of two or more propellers located inside the chamber with at least one propeller located outside the chamber at a location where the flow path enters the vessel.

Other purposes, distinctions over the art, advantages and features of the invention will be apparent to one skilled in the art upon review of the following.

DESCRIPTION OF THE PREFERRED EMBODIMENTS

Figure 1:
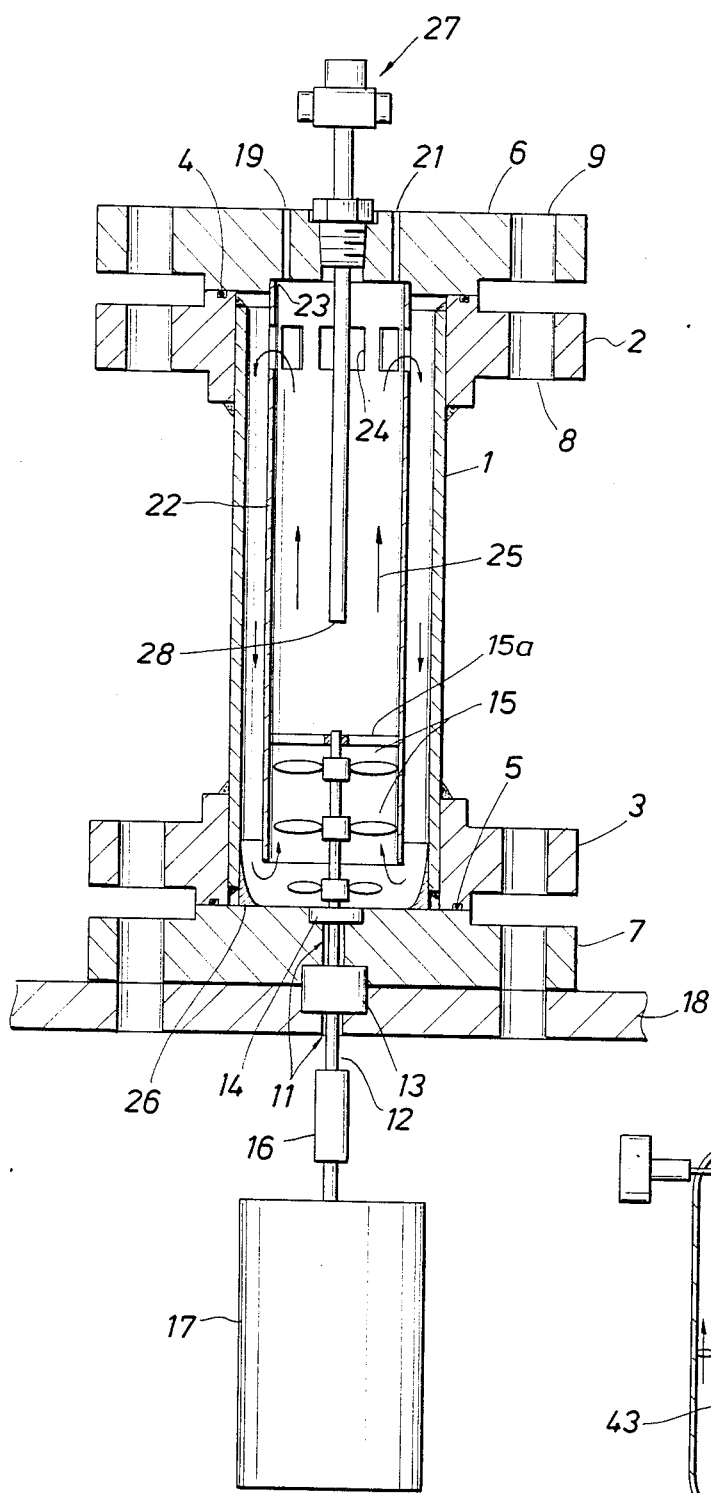
FIG. 1 discloses the viscometer assembly of the invention including the vibrating rod sensor.

The present invention provides a pressure vessel which is capable of forming a desired slurry mixture in a pressurized environment and maintaining the slurry in a relatively uniform suspension. A preferred configuration of the vessel is shown in FIG. 1. The vessel is designed to take into account the geometry and optimum operational conditions of a vibrating-rod viscosity sensor.

The pressure vessel 1 preferably comprises a cylinder such as length of pipe 1 with flanges 2 and 3 at both ends. Preferably, O-ring grooves 4 and 5 are provided in each flange. When fitted with O-rings, they form the desired pressure seal with top and bottom blind flanges 6 and 7, FIGS. 3 and 4, bolted onto the vessel flanges 2 and 3 (with bolts, not shown, through holes such as 8 and 9). The bottom flange 7 contains a liquid (e.g. $CO_2$) port-hole 10 and an opening 11 for a drive shaft 12 and bearing assembly 13 and seal assembly 14. This viscometer assembly is capable of maintaining a pressurized environment within the vessel 1 while at the same time permitting drive shaft 12 to transmit sufficient torque, at desired speeds, to the propellers 15 inside the vessel 1. Preferably, three "mix and circulate" propellers may be employed, although more or less propellers may be used as desired. The outer section of the drive shaft 12 preferably is coupled by a rigid coupling 16 to a variable speed motor 17 with a precision, speed setting potentiometer (not shown). The top flange 6 covering the vessel 1 contains intake and discharge port 19 to introduce and remove liquid (e.g. $CO_2$), etc., a temperature sensor port 20, a pressure transducer port 21, and a port 21a for a relief valve. All four ports may be used to introduce particulate (e.g. coal) into the vessel. An inner chamber, preferably a cylinder 22, is rigidly attached to the lower surface of the top flange 6 at recess 23. Cylinder 22 is suspended concentrically within pressure vessel 1 and clears its bottom flange 7 by about an inch, more or less. Two of the mixing propellers are positioned within inner cylinder 22 while the third propeller is located as close to the bottom of the vessel 1 as practicable. Circulation ports 24 are provided near the top of cylinder 22, preferably about six ports with each about one inch square.

Thus, the internal mixing system comprises the three propellers 15 and the inverted inner cylinder 22 with the circulation ports 24. The rotation of the propellers 15 mixes the slurry and, simultaneously, activates the internal circulation loop which moves the slurry upward through the inner cylinder 22, through circulation ports 24 and down an outer annulus between cylinders 22 and vessel 1, causing a pattern of circulation as shown by arrows 25. The circuit is completed when the mixture reenters the inner cylinder 22 at its base near the bottom of vessel 1. This flow pattern can be reversed by changing the direction of the propellers' rotation. The curved insert 26 at the bottom of the pressure vessel 1 and the lower-most propeller are positioned to prevent the particulate from settling in regions having a weak circulation pattern. The vessel 1 preferably is mounted on a rigid but movable table or the like, with a heavy top 18 which contains part of the bearing assembly 13 and to which the variable speed motor 17 is attached (attaching bracket not shown).

The vibrating-rod sensor, shown mounted in place, in FIG. 1, comprises a controller section 27 and a sensing element 28 made of a length of tubing (for example ½ inch stainless steel) capable of withstanding local fluid pressure. The amplitude of vibration of the probe tube 28 depends upon the viscosity of the fluid. If the fluid viscosity is high, the resistance to the shearing action of the oscillating probe tube is also high and the amplitude of the vibration is small. Conversely, if the fluid is less viscous, the amplitude will be high.

The vibrating-rod sensor of this invention is calibrated with two types of calibrations. The first is a static calibration in which the instrument is submerged in a massive, vibration-free container filled with one of several calibration fluids. The fluid is kept still during the test. The second type is a dynamic calibration which takes place in the actual apparatus under normal operating conditions.

Seal selection and the configuration of the seal-bearing arrangement 13-14 are critical to the invention. Severe requirements on the seal material and construction include small size, ability to withstand elevated temperatures, during the relatively high rotational speeds of the propellers' shaft, and ability to maintain the high pressure environment within the vessel 1. In addition, the seal must remain functional while in contact with slurries such as the highly corrosive and abrasive coal-liquid $CO_2$ mixture. A lip seal made of Nitroxile is preferred. This material is unaffected by liquid $CO_2$ and has good heat transfer characteristics. High linear speeds encountered in rotational applications generate excessive frictional heating. Elevated temperatures cause some seals, made of plastic based material, to harden. This hardening results in loss of sealing capacity as well as considerable damage to the case-hardened steel drive shaft.

A second critical area involves drive shaft misalignment. A radial and a thrust bearing are used to maintain alignment, and, to take up the thrust load on the drive shaft due to the internal pressure. More preferably, a bracket support 15a for the top of the drive shaft can be used to minimize misalignment. Any slight misalignment in the shaft overhang would be amplified by the propellers 15. Excessive vibrations would reduce the contact pressure between the shaft and the lip seal allowing coal particles to wedge themselves in that space. This usually causes the seal to fail. Therefore, misalignment at the end point of the shaft overhang must be minimized.

Figure 2A:
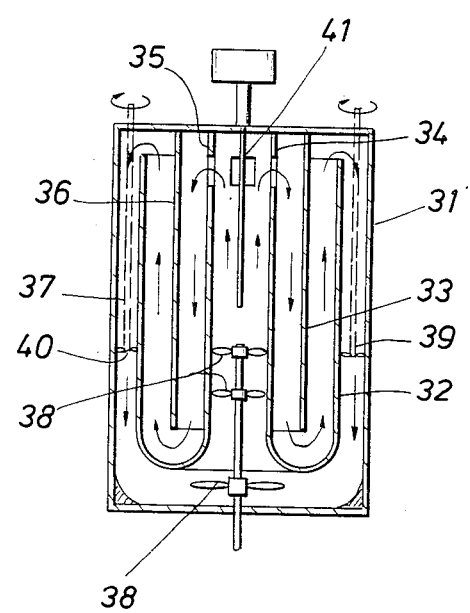
FIGS. 2A and 2B disclose other chamber geometries utilizing the same principle of flowing and simultaneous mixing.
Figure 2B:
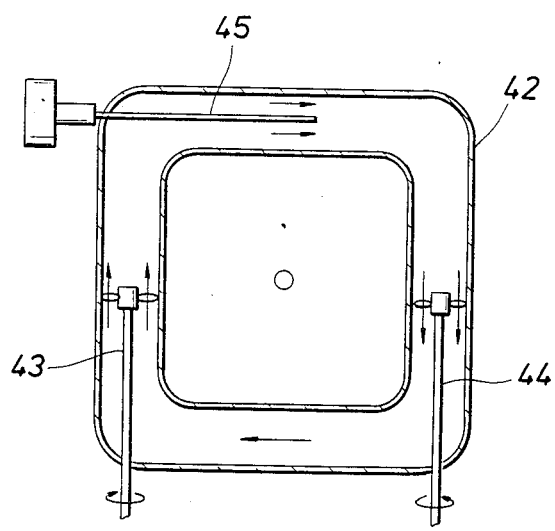

Alternative vessel geometries, utilizing the same principle of flowing and simultaneous mixing as the geometry shown in FIG. 1, are shown in FIGS. 2A and 2B. In FIG. 2A, a pressure vessel 31 contains a series of baffles 32-37, preferably cylindrical, which permit flow to proceed in the directions shown by the arrows, as caused by propellers 38-40. Similarly to the embodiment of FIG. 1 a vibrating rod sensor 41 is provided. FIG. 2B shows yet a different geometry to perform the task of simultaneous mixing and circulation. The piping arrangement 42 also permits flow in a closed loop, with the use of propellers 43 and 44. Vibrating rod sensor 45 is inserted, as in the previous embodiments so that flow is essentially parallel to the sensor. Piping arrangement 42 can be used in a stationary position or it can be made to rotate about the shown axis to assist in the initial stages of the mixing process. Similarly, the geometries in FIGS. 1 and 2A can be flipped upside down to allow gravity to assist in the initial mixing process. They can also be made to rotate about an axis perpendicular to the propeller's shaft to enhance mixing.

EXAMPLES

Testing was conducted to determine (1) the ability of the "mix and circulate" arrangement to maintain an already formed slurry in suspension, and (2) whether or not it is possible to form a slurry within the pressure vessel 1 when an amount of ground coal is first introduced in the vessel and then a corresponding amount of liquid is added on top. A full-scale plexiglass model (utilizing only a single mixing propeller) was built to permit visualization of the system operation.

Three coal-water slurry samples were prepared with coal concentrations by volume of 30%, 40% and 50%. Each one of these samples was introduced into the vessel, which operated at atmospheric conditions, and was observed to remain relatively homogeneous while the mixing propeller was in operation. Once the propeller stopped the coal tended to settle quickly. Speeds between 400 and 900 rpm appeared to be sufficient to keep the slurry stirred up. A second experiment involved the pouring of ground coal into the vessel, followed by a measured amount of naphtha. This amount forms, along with the coal, a slurry mixture which is 60% concentration by volume. Naphtha was chosen because of its superior wetting ability over water. The mixing propeller was started first at low speed and then its speed was increased while the mixing process is visually observed.

It took approximately twenty minutes for the 60% concentration coal-naphtha mixture to fluidize and for circulation to take place. Propeller speed was manipulated in order to facilitate the mixing process. By going from a low speed to a higher speed and then back to a lower speed the mixture was "jarred" into the slurry state. Several other attempts showed that operating continuously at relatively high speeds is counterproductive. The propeller creates a local circulation cell within the coal pile and the mixture does not become slurried. Operating the propeller at a uniform speed of about 800 rpm would eventually slurry the mixture but would take a longer time than with changing the speed between a low and a high value. During all attempts the viscosity sensor was continuously monitored. The completion of the mixing process was realized when the output of the sensor achieved steady state.

Figure 3:
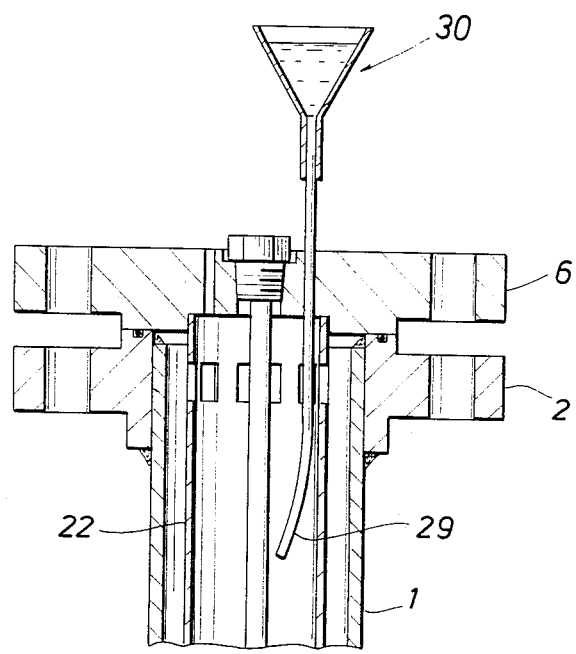
FIG. 3 discloses a typical stand pipe filling arrangement.

Measured amounts of coal were introduced into the sealed vessel via thin, flexible "stand pipes", as shown in FIG. 3. A thin-wall tube 30 was inserted into the stem of a small, glass funnel 31 and glued to it to form the stand pipe.

Figure 4:
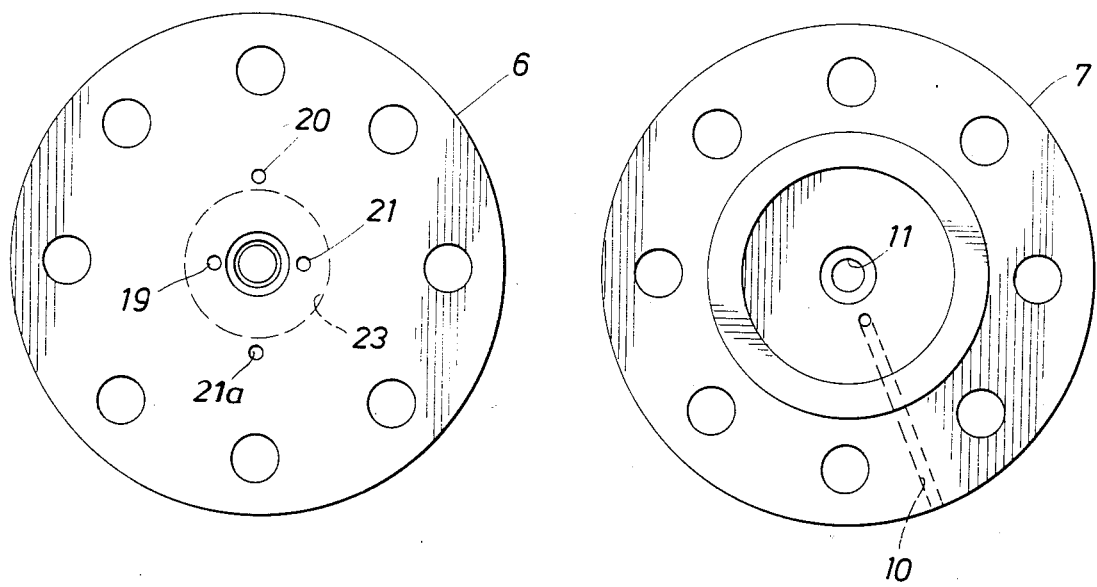
FIG. 4 discloses top and bottom flanges of the viscometer assembly of FIG. 1.

Liquid $CO_2$ was introduced into the vessel by a high pressure diaphragm pump. The pump intake was connected to a $CO_2$ cylinder and the high pressure $CO_2$ was fed through a fitting in the bottom flange of the vessel, as shown in FIG. 4, in order to help fluidize the packed coal.

Coal samples from the Young's Creek mine in Montana, core #875 at 31 ft. were used. The coal was first crushed to $\frac{1}{4}''\times 0$, then ground in a hammer mill with a 0.027" slotted screen. To determine the correct amounts of coal needed for each slurry concentration, the capacity of the pressure vessel must be known. It was obtained by measuring the volume of the amount of liquid which would fill the vessel completely with all components in place.

The following procedures describe the steps taken to conduct one experimental run which generates one data point.

After cleaning and assembly, the system was readied to measure the apparent viscosity of a sample mixture of coal-liquid $CO_2$ with a particular volume concentration. An amount of powdered coal, which corresponds to that volume concentration, was introduced into the pressure vessel. This was done in such a way as to distribute the coal as evenly as possible within the vessel. The four openings which were machined into the top flange, as shown in FIG. 4, were used as coal ports. A small amount of coal was introduced via the flexible stand pipe 29 and funnel 30 (FIG. 3), sequentially, at each port. Care was taken not to lose any coal during the filling process in order to preserve the predetermined volume concentration assigned to this particular test run. After the vessel was loaded with coal, the following connections were made to the ports on the top flange:

1. A strain gauge-type pressure transducer was directly mounted on one port.
2. A thermocouple-type thermometer probe was inserted into a second port and secured by a pressure fitting.
3. The third port was sealed by an adjustable relief valve rated for 1500 psi.
4. The last port was connected to the high pressure $CO_2$ pump with appropriate gauges, valves and venting bypasses.

The $CO_2$ port in the bottom flange 7 was also connected to the pump with similar provisions. The vessel was charged with $CO_2$ through the bottom flange port, and, $CO_2$ was released through the top flange connection. Two special valves were mounted on these $CO_2$ lines, as close to the body of the vessel as possible, in order to isolate the vessel, during the actual test, from the rest of the system.

The next step was to introduce the $CO_2$ charge. A new $CO_2$ bottle was used for each run. It was mounted upside down on a scale and connected to the intake of the $CO_2$ pump via a flexible high pressure hose. The pressure vessel was first sealed off and the $CO_2$ cylinder fully opened to allow the piping system to be filled up with $CO_2$. The weight of the $CO_2$ cylinder was registered at this time followed by the opening of the intake valve which was mounted on the bottom flange, to allow $CO_2$ to fill the vessel at cylinder pressure. Additional $CO_2$ was pumped into the vessel until the desired pressure was reached. The pump was then shutoff, the vessel sealed and the $CO_2$ cylinder weighed again. The difference between the two weights gave the amount of $CO_2$ introduced into the pressure vessel. At this juncture, the pressure vessel was considered charged with the proper amounts of coal and liquid $CO_2$, and the mixing process began.

After the slurry was formed, voltages were read representing the outputs of the viscosity sensor, the pressure transducer and the thermocouple probe. Also, the propellers' RPM was noted. The output voltages of the viscosity detector and the pressure transducer were also recorded continuously on a chart recorder for reference.

It was concluded that the present invention provides a relatively quick and cost effective method for determining viscosities of conventional and unconventional slurries. The system can be used as a screening device to obtain slurry viscosities for different solids, carrier fluids and at different concentrations and particle size distributions. The viscometer permits in situ slurry formation and dynamically maintained suspension and mixing.

The foregoing description of the invention is merely intended to be explanatory thereof, and various changes in the details of the described method and apparatus may be made within the scope of the appended claims without departing from the spirit of the invention.

What is claimed is:

1. An apparatus for measuring slurry viscosity, comprising:
   a vessel defining a closed loop flow path which is formed by at least one chamber within the vessel, the chamber having a top, bottom and sides, with the top and bottom being at least partially open and the sides being at least partially spaced from the vessel;
   means for the simultaneous formation and circulation of the slurry through the closed loop flow path; and
   means for measuring the viscosity of the slurry as the slurry flows in the flow path.

2. The apparatus of claim 1 wherein the chamber has circulation ports at its top and is open at its bottom.

3. The apparatus of claim 1 wherein the means for flowing the slurry is at least one propeller located within the chamber.

4. The apparatus of claim 1 wherein the means for flowing the slurry is several propellers located within the chamber with at least one propeller located outside the chamber at a location which assists the circulation and mixing of the slurry.

5. An apparatus for measuring slurry viscosity, comprising:
   a vessel defining a closed loop flow path which is formed by a series of baffles;
   means for the simultaneous formation and circulation of the slurry through the closed loop flow path; and
   means for measuring the viscosity of the slurry as the slurry flows in the flow path.

6. An apparatus for measuring slurry viscosity, comprising:
   a vessel defining a closed loop flow path which is a piping arrangement;
   means for rotating the piping arrangement about an axis which assists mixing of the slurry;
   means for the simultaneous formation and circulation of the slurry through the closed loop flow path; and
   means for measuring the viscosity of the slurry as the slurry flows in the flow path.

7. The apparatus of claim 1, 5 or 6 wherein the slurry comprises a carrier liquid and a ground solid particulate.

8. The apparatus of claim 1, 5 or 6 wherein the particulates are any non-dissolving solid material ground to an appropriate particle size distribution suitable for slurrying and slurry transport.

9. The apparatus of claim 1, 5 or 6 wherein the slurry comprises a carrier liquid and a ground solid particulate and the liquid is selected from a fluid which is a liquid at standard temperature and pressure or from a liquefied gas which is maintained at an elevated pressure.

10. The apparatus of claim 1, 5 or 6 wherein the means for measuring the viscosity of the slurry is a vibrating-rod sensor.

11. A method for measuring slurry viscosity, comprising:
    flowing the slurry in a closed loop flow path;
    inserting a vibrating-rod sensor into the flowing slurry; and
    correlating the viscosity of the slurry to amplitude of vibration of the vibrating-rod sensor.

12. The method of claim 11 wherein the slurry is flowed through a chamber within a vessel and between the vessel and the chamber.

13. The method of claim 12 wherein the slurry is flowed by means of several propellers of which at least one is located inside the chamber and at least one is outside the chamber at a location to improve circulation and mixing.

14. The method of claim 11 wherein the slurry is flowed through a circuitous closed loop path formed by baffles.

15. The method of claim 11 wherein the slurry is flowed through a piping arrangement forming the closed loop path.

16. The method of claim 15 wherein the piping arrangement is rotated about an axis which assists mixing the slurry.

* * * * *